United States Patent [19]

Gosselin

[11] Patent Number: 4,885,728
[45] Date of Patent: Dec. 5, 1989

[54] ELECTRICAL WRIST BAND CONNECTOR FOR A WATCH BAND

[75] Inventor: Jerome T. Gosselin, Round Rock, Tex.

[73] Assignee: Minnesota Mining and Manufacturing Company, St. Paul, Minn.

[21] Appl. No.: 61,911

[22] Filed: Jun. 11, 1987

[51] Int. Cl.⁴ ............................................. H05F 3/00
[52] U.S. Cl. ...................................... 368/10; 361/212; 361/220; 439/92; 439/98; 439/420; 439/799
[58] Field of Search .................. 174/78; 361/212, 220; 439/92, 98, 100, 420, 444, 799

[56] References Cited

U.S. PATENT DOCUMENTS 3,340,630  9/1967  Becker ..................................... 40/21
4,677,521  6/1987  Frazier ................................. 361/220

*Primary Examiner*—Bernard Roskoski
*Attorney, Agent, or Firm*—Donald M. Sell; Walter N. Kirn; John C. Barnes

[57] ABSTRACT

A wrist band connector constructed from a sheet of deformable, electrically conductive material having tabs at both ends capable of being folded around a wrist band and an electrical connection mechanism mechanically and electrically attached to the sheet between the tabs and providing an electrical connection point for an electrical cable, as for example, an electrical ground cord. An outer insulative layer may be provided and tangs may be formed into the tabs to provide additional assurance that intimate electrical contact will be made with the interior surface of the wrist band onto which the wrist band connector is installed.

4 Claims, 2 Drawing Sheets

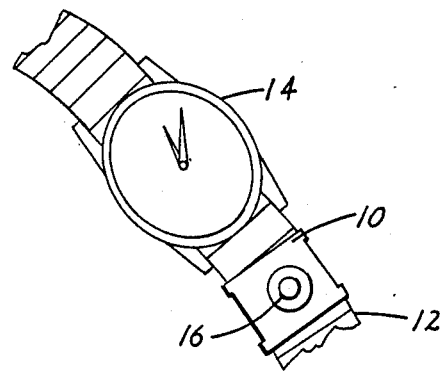
FIG. 1
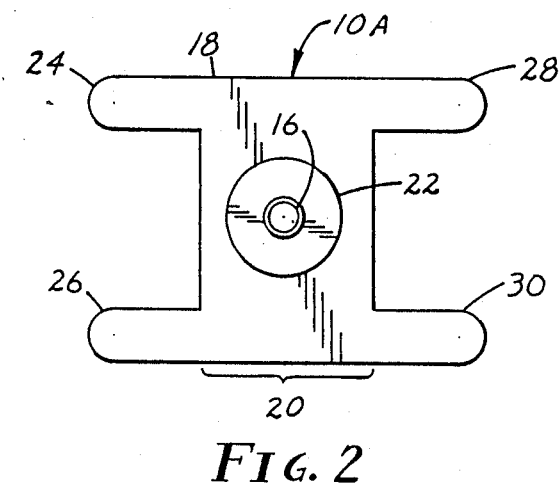 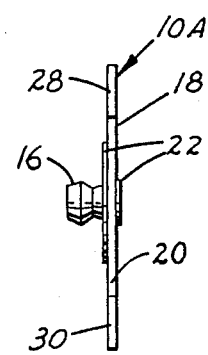
FIG. 2  FIG. 3

ELECTRICAL WRIST BAND CONNECTOR FOR A WATCH BAND

BACKGROUND OF THE INVENTION

The present invention relates generally to electrostatic grounding equipment and particularly to body straps intended to be worn by individuals to prevent the accumulation of electrostatic changes.

Generally, a need exists for devices to control the electrostatic charge accumulation on the body or person of an individual. Certain individuals occupy areas or handle materials in which an electrostatic discharge could either be hazardous to the individual or could damage the material being handled. Examples are individuals in the proximity of an explosive or hazardous environment and indivduals who must handle electostatic sensitive electronic components.

Many devices have been developed to solve the problem of electrostatic charge accumulation and subsequent discharge. These include devices which have been fastened into body straps or wrist straps to be worn by the particular individual involved. These body straps or wrist straps are then adapted to be connected to a ground potential, possibly through a predetermined resistance, in order to dissipate the electrostatic charge accumulation on the individual and to prevent additional electrostatic charge accumulation. These devices operate by draining off any accumulated electrostatic charge from the individual.

One of these devices is the model 2064 wrist strap manufactured by Minnesota Mining and Manufacturing Company (3M), St. Paul, Minn. The model 2064 wrist strap consists of a Velostat (Velostat is a trademark of the 3M Company) strip held on the wrist with a band of nylon. Velostat conductive material is a carbonloaded conductive polymer. The operation of the wrist strap relies on the conductive polymer to conduct electrostatic charge via the individual's wrist to a ground cord secured to the wrist strap with an electrically conductive snap connection. The wrist strap relies on a hook and loop fastener system (e.g., Scotchmate, a trademark of 3M, fastener or Velcro, a trademark of Velcro U.S.A., Inc., Manchester, N.H., fastener) to secure the wrist strap to the wrist of the individual wearer.

A wrist strap manufactured by Semtronics Corporation, Peachtree City, Ga., is constructed from similar functional components. The Semtronics wrist strap also uses a black conductive plastic secured to the wrist with a hook and loop closure system.

A wrist strap manufactured by Simco, Landsdale, Pa., also uses a similar system. The entire band of the wrist strap is made of a nylon hook and loop fastener system. The Simco wrist strap has a carbonloaded conductive material secured to the inner surface of the hook and loop fastener. A snap connection is provided for a ground cord. The Simco wrist strap again relies on the conductive polymer for conducting the electrostatic accumulation on the individual to the snap connection and to the grounding cord. Similarly, the Simco wrist strap also relies on the hook and loop fastener for the closure system.

A wrist strap manufactured by Wescorp of Mountainview, Calif., consists of a carbonloaded conductive fabric with a hook and loop fastener. The Wescorp wrist strap relies on the conductive fabric for the conduction of electrostatic charge from the individual instead of the conductive polymer as in the previous straps but again relies on the hook and loop fastener for the closure system. The Wescorp strap also utilizes the conductive fabric for a connection to ground rather than a connection point to a ground wire.

A strap manufactured by Walter G. Legge Company, New York, N.Y., carrying the name "WRISTSTAT" uses a black nylon band with a hook and loop fastener. A conductive polymer is attached to the band with a metallic plate at a relatively narrow location around the strap. The conductive polymer also has a snap connection to a ground cord. The Legge wrist strap relies on the middle plate and the conductive polymer for conductivity and relies on the nylon band with the hook and loop fastener for the closure system.

Wescorp also has a strap consisting of a metallic bead chain to which an electrical ground cord is slidably attached. The strap relies on the metallic beads for conductivity. Since it is worn loosely around the wrist, it can be made large enough to slip over the hand onto the wrist and, thus, no detachable closure is required.

Controlled Static Company, Santa Fe, Calif., manufactures a wrist strap known in the trade as a Fred strap. The strap is a metallic expansion band having a snap connection for an electrical ground cord. The band is reminiscent of a metallic expansion watch band. The band relies on the conductivity of the metal for the drainage of the accumulated electrostatic charges and will expand to slip on the wrist over the hand and then fit relatively snuggly.

U.S. Pat. No. 4,398,277, Christiansen et al, assigned to 3M, discloses a conductive elastomeric fabric and body strap constructed from that fabric. In a preferred embodiment in Christiansen et al, a wrist strap is formed utilizing a knit fabric having electrically conductive fibers and elastomeric fibers as well as an insulative fiber. The knit band is constructed with the electrically conductive fibers on the inner surface, the insulative fibers on the outer surface and with the elastomeric fibers allowing for extensibility of the strap.

U.S. Pat. No. 4,577,256, Breidegam, assigned to Semtronics Corporation, Peachtree City, Ga., describes a woven stretchable grounding strap. The strap has conductive fibers on the inside surface of the strap to contact the skin and conduct electrical charges to a grounding cord attached to the strap. An adjustable mechanical clasp is provided to provide an adjustable sized wrist strap.

All of the above wrist straps provide a mechanism for draining accumulated electrostatic charges from the body of the wearer of the wrist strap. All of the wrist straps provide an electrically conductive surface in contact with the wrist, a mechanical closure system for closing the strap around the wrist and a point for the electrical connection of a ground cord. All of the above described wrist straps, however, are relatively expensive to construct since they all must fit around the wrist and require the wearer to place a strap around his wrist in addition to a watch band he may be currently wearing.

U.S. Pat. No. 3,546,800, Tate, Jr., discloses one of a variety of known calendar attachments for a wrist watch band. As described in Tate, Jr., such calendar attachments are formed from a flat plate of a soft flexible metal which can be manually wrapped around the wrist watch band and bent into place to clamp the band and having a central portion onto which is printed indicia representing a calendar. While such devices are effective in providing ready access to a calendar for the wearer of a watch band, the device has absolutely nothing to do with the electostatic charge buildup on the wearer.

SUMMARY OF THE INVENTION

The present invention solves the problem of having to provide a complete wrist strap for someone who is trying to achieve the function of draining accumulated electrostatic charges from his body. This solution is useful when the individual is already wearing a wrist band which has a conductive inner surface contacting the body, e.g., the wrist, of the wearer such as a watch band connected to a watch. Instead of requiring the wearer to wear a completely separate band, in addition to his wrist watch band, the present invention allows the wearer to utilize the conductive inner surface of the watch band and simply provides a wrist band connector which attaches to the electrically conductive inner surface of the watch band. The wrist band connector has an electrical connection mechanism mechanically affixed to a central portion of the connector which provides a connection point for the attachment of an electrical cord which can be adapted to be connected to electrical ground. The wrist band connector can be folded around the existing watch band of the wearer with the wrist band connector making electrical contact with the inner conductive surface of the watch band. Thus, the connector operates by providing a conduit between the inner conductive surface of the watch band and an external electrical ground cord. Thus, only one wrist band connector need be utilized and an increased amount of comfort is provided to the user.

The present invention provides a wrist band connector which has a sheet of deformable, electrically conductive material having tabs at both ends capable of being folded around a wrist band and an electrical connection mechanism mechanically and electrically attached to the sheet between the tabs for providing an electrical connection point for an electrical cable. It is preferred that the deformable, electrically conductive material be constructed from metal. It is further preferred that a layer of electrically insulative material be applied to the outside surface of the sheet of deformable electrically conductive material. In one embodiment, the electrically insulative material is an electrically insulative coating. In one embodiment, the electrical connection mechanism is a snap connector.

The present invention also provides a wrist band connector having a sheet of deformable, electrically conductive material having tabs at both ends capable of being folded around a wrist band with each of the tabs having a plurality of tangs projecting from the surface of one side of the sheet and having electrical connection means mechanically and electrically attached to the sheet between the tabs providing an electrical connection point for an electrical cable to the wrist band connector. It is preferred that the sheet of deformable electrically conductive material be constructed from metal. It is also preferred that the wrist band connector have a layer of electrically insulative material applied to the exterior surface of the wrist band connector. In one embodiment, the electrically insulative material is an electrically insulative coating. In one embodiment, the electrical connection mechanism is a snap connector.

BRIEF DESCRIPTION OF THE DRAWINGS

The foregoing advantages, construction and operation of the present invention will become more readily apparent from the following description and accompanying drawings in which:

FIG. 1 is a perspective view of a wrist band connector of the present invention installed on a watch band;

FIG. 2 is a top view of one embodiment of wrist band connector of the present invention;

FIG. 3 is an edge view of the wrist band connector of FIG. 2;

DETAILED DESCRIPTION OF THE PREFERRED EMBODIMENTS

Figure 4:
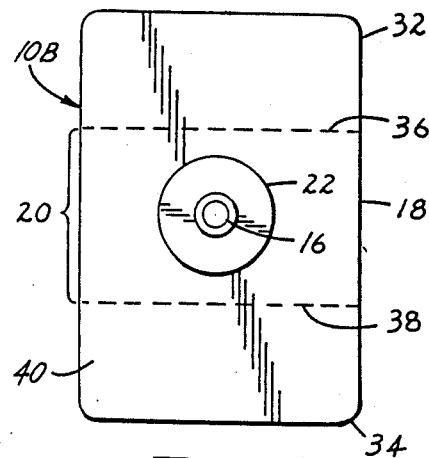
FIG. 4 is a top view of an alternative embodiment of a wrist band connector of the present invention.

As FIG. 1 illustrates, the wrist band connector 10 of the present invention may be utilized with existing conventional watch bands 12 without the necessity of having a separate wrist band for the sole purpose of providing protection against electrostatic charge accumulation. The wrist band connector 10 is shown attached to a watch band 12 which holds a watch 14 onto the wrist (not shown) of a wearer. The wrist band connector 10 has a snap connector 16 located in the central part of the wrist band connector 10 facilitating the connection of an electrical ground cord (not shown) which can be utilized by the user of the wrist band connector 10 to prevent the accumulation or to allow for the drainage of accumulated electrostatic charges. It is preferred that the electrical ground cord attached to the snap connector 16 contain a current limiting resistor providing an overall resistance from the wrist of the user to electrical ground of approximately 1 megohm. This will help protect the user in the event of accidental contact by the user to high voltage source. The wrist band connector 10 is formed around watch band 12 making electrical contact with the interior surface of watch band 12. It is very strongly preferred that for the proper functioning of wrist band connector 10 that the interior surface of watch band 12 be electrically conductive. This will allow the contact of the watch band 12 around a substantial portion of the circumference of the wrist of the user and, hence, allowing for a substantial number of electrical contact points and insuring good electrical continuity between the watch band 12, wrist band connector 10 and ultimately the electrical ground cord. Wrist band connector 10 makes electrical contact with the watch band 12 also on the exterior surface of the watch band 12 if the watch band 12 is electrically conductive on the exterior surface. This would be true, for example, for commonly available metal watch bands which can be either of the expansion variety or clasp variety.

FIGS. 2 and 3 illustrate one embodiment of the wrist band connector 10A of the present invention. Wrist band connector 10A is comprised of a sheet 18 of a deformable, electrically conductive material. It is preferred that the sheet 18 be constructed from a flat plate of soft flexible metal such as aluminum. As an example, the sheet 18 may be constructed from soft aluminum stock approximately 0.015 inch (0.38 millimeters) in thickness. Sheet 18 has a central portion 20 upon which is attached snap connector 16. Snap connector 16 is mechanically and electrically affixed to sheet 18 by rivet 22. Tabs 24 and 26 project from one end of sheet 18 and are intended to be bent by the user around one side of the watch band 12 as illustrated in FIG. 1. Tabs 28 and 30 project from the opposite end of sheet 18 and are also intended to be bent by the user around the opposite side of watch band 12 also as illustrated in FIG. 1.

Figure 5:
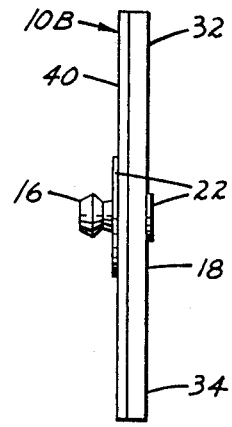
FIG. 5 is an edge view of the wrist band connector of FIG. 4.

FIGS. 4 and 5 represent an alternative embodiment of a wrist band connector 10B of the present invention. Wrist band connector 10B is also constructed from a sheet 18 of deformable electrically conductive material. Sheet 18 also has a central portion 20 to which snap connector 16 is affixed again by rivet 22. Wrist band connector 10B has tabs 32 and 34, both extending the width of sheet 18 on opposite ends of sheet 18 and both capable of being formed around the edges of a watch band 12 as shown by the imaginary fold lines 36 and 38. Since the wrist band connector 10B can be utilized on a watch band 12 which has an exterior electrically nonconductive surface it is desirable that the wrist band connector 10B also have an exterior surface which is electrically nonconductive, i.e., electrically insulative, when the electrical ground cord is placed on top of snap connector 16. Thus, wrist band connector 10B has a layer 40 of an electrically insulative material applied to the exterior side of sheet 18 to provide an electrically insulative exterior surface. It is preferred that layer 40 be a coating of an electrically insulative material such as a 0.001 inch (0.025 millimeter) thick coating of lacquer. Layer 40 could also be an anodized surface on sheet 18.

Figure 6:
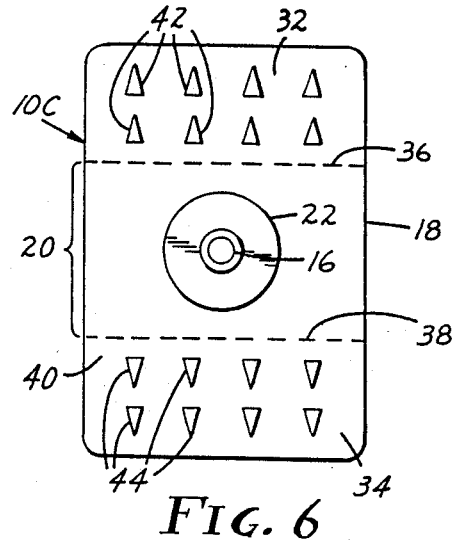
FIG. 6 is a top view of an alternative embodiment of a wrist band connector of the present invention.
Figure 7:
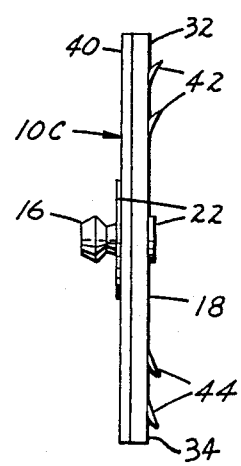
FIG. 7 is an edge view of the wrist band connector of FIG. 6.

The wrist band connector 10C as illustrated in FIGS. 6 and 7 is identical to the wrist band connector 10B illustrated in FIGS. 4 and 5 with the exception that tangs 42 are formed in tab 32 and tangs 44 are formed in tab 34. The wrist band connector 10C can be utilized on cloth watch bands which contain an interior conductive surface or on existing fabric wrist band which are already intended for electrostatic charge dissipation. Tangs 42 and 44 are formed in sheet 18 by stamping triangular portions and bending the tangs inward to form a plurality of projections from tabs 32 and 34 respectively. In a preferred embodiment, tangs 42 and 44 are approximately 0.09 inches (2.3 millimeters) long, approximately, 0.09 inches (2.3 millimeters) wide at the base and project approximately 0.06 inches (1.5 millimeters) from the surface of sheet 18.

Figure 8:
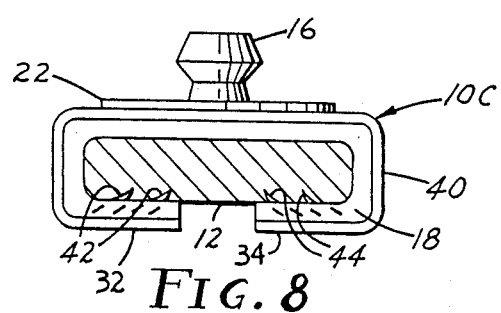
FIG. 8 is a side view showing the wrist band connector of FIGS. 6 and 7 installed on a watch band.

FIG. 8 shows wrist band connector 10C installed around a fabric watch band 12. Tangs 42 and 44 bite into the inner conductive part of watch band 12 providing good electrical contact to the interior surface of watch band 12.

Thus, there has been shown and described a novel wrist band connector. It is to be recognized and understood, however, that various changes, modifications and susbstitution in the form and of the details of the present invention can be made by those skilled in the art without departing from the scope of the following claims.

What is claimed is:

1. A wrist band connector affording electrical connection between a conductive wrist band and an electrical ground cable, said connector comprising:
   a sheet of deformable conductive metal having opposite surfaces and a central portion defined by sides and ends and integrally formed tabs positioned one on each side of said central portion, which tabs are foldable about the edges of a said wrist band for retaining said central portion on one surface of the band and for making electrical contact with the band, and
   a snap electrical connector mounted on one surface of said sheet and means for mechanically and electrically mounting said connector to said central portion of said sheet between said sides and ends for providing an electrical connection for a said cable to said sheet.

2. A wrist band connector according to claim 1 wherein said sheet has a layer of electrically insulative material applied to said one surface of said sheet.

3. A wrist band connector according to claim 2 wherein said tabs have tangs formed thereon which tangs project from the surface of said sheet opposite said one surface of said sheet affording electrical contact with a wrist band.

4. A wrist band connector according to claim 1 wherein the metal is a soft deformable aluminum.

* * * * *